US009011930B2

(12) United States Patent
Scaffidi

(10) Patent No.: US 9,011,930 B2
(45) Date of Patent: Apr. 21, 2015

(54) NUTRITIONAL SUPPLEMENT AND USE THEREOF

(75) Inventor: James Scaffidi, Shrewsbury, MA (US)

(73) Assignee: ZyCal Bioceuticals Healthcare Company, Inc., Shrewsbury, MA (US)

( * ) Notice: Subject to any disclaimer, the term of this patent is extended or adjusted under 35 U.S.C. 154(b) by 469 days.

(21) Appl. No.: 11/414,871

(22) Filed: May 1, 2006

(65) Prior Publication Data

US 2007/0254040 A1 Nov. 1, 2007

(51) Int. Cl.
*A61K 35/32* (2006.01)
*A61K 31/4188* (2006.01)
*A61K 31/455* (2006.01)
*A61K 38/18* (2006.01)
*A61K 47/46* (2006.01)

(52) U.S. Cl.
CPC ............. *A61K 35/32* (2013.01); *A61K 38/1875* (2013.01); *A61K 47/46* (2013.01); *Y10S 530/84* (2013.01); *A61K 31/4188* (2013.01); *A61K 31/455* (2013.01); *A61K 38/18* (2013.01)

(58) Field of Classification Search
None
See application file for complete search history.

(56) References Cited

U.S. PATENT DOCUMENTS

| | | | |
|---|---|---|---|
| 3,845,770 A | 11/1974 | Theeuwes et al. | |
| 3,995,631 A | 12/1976 | Higucki et al. | |
| 4,034,756 A | 7/1977 | Higuchi et al. | |
| 4,111,202 A | 9/1978 | Theeuwes | |
| 4,290,426 A | 9/1981 | Luschen et al. | |
| 4,320,759 A | 3/1982 | Theeuwes | |
| 4,327,725 A | 5/1982 | Cortese et al. | |
| 4,394,370 A | 7/1983 | Jefferies | |
| 4,427,583 A | 1/1984 | England et al. | |
| 4,434,094 A | 2/1984 | Seyedin et al. | |
| 4,440,750 A | 4/1984 | Glowacki et al. | |
| 4,449,983 A | 5/1984 | Cortese et al. | |
| 4,455,256 A | 6/1984 | Urist | |
| 4,470,840 A | 9/1984 | Welebir | |
| 4,563,489 A | 1/1986 | Urist | |
| 4,596,574 A | 6/1986 | Urist | |
| 4,627,982 A | 12/1986 | Seyedin et al. | |
| 4,678,470 A | 7/1987 | Nashef et al. | |
| 4,765,989 A | 8/1988 | Wong et al. | |
| 4,767,627 A | 8/1988 | Caldwell et al. | |
| 4,774,228 A | 9/1988 | Seyedin et al. | |
| 4,774,322 A | 9/1988 | Seyedin et al. | |
| 4,810,691 A | 3/1989 | Seyedin et al. | |
| 4,839,177 A | 6/1989 | Colombo et al. | |
| 4,843,063 A | 6/1989 | Seyedin et al. | |
| 4,851,232 A | 7/1989 | Urquhart et al. | |
| 4,871,548 A | 10/1989 | Edgren et al. | |
| 4,877,864 A | 10/1989 | Wang et al. | |
| 4,892,778 A | 1/1990 | Theeuwes et al. | |
| 4,915,949 A | 4/1990 | Wong et al. | |
| 4,940,465 A | 7/1990 | Theeuwes et al. | |
| 5,007,790 A | 4/1991 | Shell | |
| 5,013,649 A | 5/1991 | Wang et al. | |
| 5,126,142 A | 6/1992 | Ayer et al. | |
| 5,256,440 A | 10/1993 | Appel et al. | |
| 5,443,843 A | 8/1995 | Curatolo et al. | |
| 5,534,263 A | 7/1996 | Wong et al. | |
| 5,582,837 A | 12/1996 | Shell | |
| 5,780,057 A | 7/1998 | Conte et al. | |
| 6,136,795 A * | 10/2000 | Florio .............................. 514/62 |
| 6,344,437 B1 | 2/2002 | Takada et al. | |
| 6,797,283 B1 | 9/2004 | Edgren et al. | |
| 2003/0032098 A1* | 2/2003 | Young et al. ................. 435/69.1 |

FOREIGN PATENT DOCUMENTS

| | | |
|---|---|---|
| RO | 90405 | 10/1986 |
| WO | WO 90/11366 | 10/1990 |
| WO | WO 91/18098 | 11/1991 |
| WO | WO 99/07342 | 2/1999 |

OTHER PUBLICATIONS

Maddox et al. "Optimizing Human Demineralized Bone Matrix for Clinical Application" Tissue Engineering Aug. 2000, vol. 6 (4) 441 (Abstract Only).*
NCI Drug Dictionary, Def "demineralized bone matrix" www.cancer.gov/Templates/drugdictionary.aspx?CdrID=476316, 1 pg.*
Endogenous: Definition from Answers.com, http://www.answers.com/topic/endogenous?&print=true, accessed Mar. 10, 2010 4 pgs.*
Tripodi "The Osteoinductive Effects of Cyplexinol in the Effective Management of Osteoporosis: A Case Study", Integrative Medicine • vol. 12, No. 5 • Oct. 2013.*
Garian—2012 "An Osteoinductive Protein Complex That Stimulates Regeneration of Bone and Cartilage for Treatment of Moderate to Severe Osteoarthritis", Integrative Medicine • vol. 11, No. 5 • Oct. 2012.*
Garian—2013 "Evaluating Clinical Response and Activity of Cyplexinol Osteoinductive Proteins in Osteoarthritis of the Hip and Knee: A Randomized, Controlled Trial" Integrative Medicine • vol. 12, No. 2 • Apr. 2013.*
ZyCal Bioceuticals Healthcare Co. "Ostinol:Clinical Efficacy" 8 pgs received Jan. 15, 2015.*
Urist, MR. Bone: "Formation by Autoinduction", Science 1965; pp. 150:893-9.

(Continued)

*Primary Examiner* — Thane Underdahl
(74) *Attorney, Agent, or Firm* — Ralph T. Lilore

(57) ABSTRACT

Nutritional supplements and methods for maintaining and/or improving the condition of bones or cartilage in a mammal, particularly a human. One such supplement comprises demineralized bone matrix (DBM) wherein the DBM comprises a bone growth improving amount of at least one osteoinductive growth factor. A preferred supplement composition further comprises at least one vitamin, such as vitamin E. One method comprises orally administering to the mammal on a periodic basis a supplement comprising DBM. In a preferred method the DBM composition is periodically administered and there is a further periodic administration of a therapeutically effective amount of a calcium-containing composition; the calcium-containing composition is administered temporally spaced apart from said DBM composition for maximum effectiveness.

14 Claims, No Drawings

(56) References Cited

OTHER PUBLICATIONS

Urist, MR, Iwata H, Cecotti PL, et al. "Bone Morphogenesis in Implants of Insoluble Bone Gelatin", Proc. Natl. Acad. Sci. USA 1973; pp. 70:3511-15.

Urist MR, Mikulski A, Lietze A. "Solubilized and Insolubilized Bone Morphogenetic Protein", Proc. Natl. Acad. Sci. USA 1979 vol. 76: pp. 1828-1832.

Tye CE, Hunter GK, Goldberg HA. "Identification of the Type I Collagen-Binding Domain of Bone Sialoprotein and Characterization of the Mechanism of Interaction", J. Biol. Chem. 2005 vol. 280; pp. 13487-13492.

Damien Christopher J. et al., "Purified Bovine BMP Extract and Collagen for Spine Arthrodesis, Preclinical Safety and Efficacy", Spine 2002; vol. 27; pp. S50-S58.

Wozney JM. "Overview of Bone Morphogenetic Proteins", Spine 2002 vol. 27(16S); pp. S2-S8.

Sampath TK, Reddi AH. "Distribution of Bone Inductive Proteins in Mineralized and Demineralized Extracellular Matrix", Biochem. Biophy. Res. Comm. 1984;vol. 119(3): pp. 949-954.

Boden SD, Grod D, Damien C., "Ne-Osteo Bone Growth Factor for Posterolateral Lumbar Spine Fusion: Results From a Nonhuman Primate Study and a Prospective Human Clinical Pilot Study", Spine 2004; vol. 29(5): pp. 504-514.

Huggins, Arch. Surg. (1931), vol. 22, pp. 377-408.

Urist, Science (1965), vol. 150, pp. 893-899.

Reddi et al., Proc. Nat. Acad. Sci. USA (1972), vol. 69, No. 6, pp. 1601-1605.

Urist et al., Proc. Nat. Acad. Sci. USA (1979), vol. 76, No. 4, pp. 1828-1832.

Mulliken et al., Plast. Reconstr. Sug. (1980), vol. 65, No. 5, pp. 533-559.

Glowacki et al., Lancet (May 2, 1981), pp. 959-962.

Shin, H.I. et al., Key Engineering Materials (2005), vols. 288-289, pp. 249-252.

Benya, et al., Cell (1982), vol. 30, pp. 215-224.

Renard, et al., Anal Biochem (1980), vol. 104, pp. 205-214.

Renard, et al., Arch Biochem Biophys (1981), vol. 207, No. 2, pp. 399-406.

Seyedin, et al., J Cell Biol (1983), vol. 97, pp. 1950-1953.

Shures, et al., Clinical Chimica Acta (1977), vol. 81, pp. 1-40.

Berry, et al., J Exp Med (1961), vol. 114, No. 5, pp. 761-777.

Khosla and Davis, International Journal of Pharmaceutics (1990), vol. 62, pp. R9-R11.

Coupe et al., Pharmaceutical Research (1991), vol. 8, No. 10, pp. 1281-1285.

Timmermans et al., Journal of Pharmaceutical Sciences (1993), vol. 82, No. 8, p. 854.

Conte et al., J. Controlled Release (1993), vol. 26, pp. 39-47.

Krinsky, Ann. Rev. Nutr. (1993), vol. 13, pp. 561-587.

J.A. Martinez, M. Elorriaga, M. Marquinez, J. Larralde; Skeletal Growth after Oral Administration of Demineralized Bone Matrix; Revista Espanola De Fisiologia, 49 (1), 37-42, 1993, Spain.

* cited by examiner

NUTRITIONAL SUPPLEMENT AND USE THEREOF

BACKGROUND OF THE INVENTION

The present invention is directed to compositions useful as nutritional supplements and to methods of improving the well being of mammals ingesting such compositions, particularly their ability to assist in the production, maintenance and repair of bone and bone structures in the body.

Derivatives of collagen and bone have long been used in the surgical repair of bone defects and bone trauma in mammals. For example, in 1899, Senn showed healing of experimental canine calverial defects and of human tibial and femoral defects with decalcified ovine bone. Others have shown bone formation in periapical areas in dogs and monkeys and in skull defects in rats after implantation or demineralized bone by itself. The osteogenic potential of demineralized bone powder has been demonstrated in cranial osseous defects in rats.

In 1931, Huggins (Arch. Surg., 22:377-408) reported that proliferating mucosa of Kidney, ureter, or bladder induced bone formation when implanted in connective tissue. This was the first reported experimental model of induced ectopic osteogenesis. More recently, Urist (Science, 150: 893-899, 1965) and Reddi et al (Proc. Natl. Acad. Sci. U.S.A., 69: 1601-1605, 1972) demonstrated that osteogenesis could also be induced by the acellular, demineralized matrix of bone or dentin. It has been shown that physical factors, including surface charge and geometry of the matrix, are involved, Reddi et al (Proc. Natl. Acad. Sci. U.S.A., 69: 1601-1605, 1972). There is evidence that a soluble factor from demineralized bone, bone morphogenetic protein, is osteoinductive; see Urist et al, Proc. Natl. Acad. Sci. U.S.A., 76: 1828-1932, 1979. Thereafter, Mulliken reported on the use of demineralized bone segments, chips, and powder for reconstruction of craniofacial defects in rats and humans; see Mulliken et al. Plast. Reconstr. Surg., 65: 533-559, 1980 and Glowacki et al, Lancet, May 2, 1981, 963-966. Furthermore, the glycoprotein, bone morphogenetic protein (BMP), has been characterized and is reported to have induced new bone formation in rats. Additionally, BMP's action does not appear to be species-specific; rabbit BMP has induced new bone formation in rats and bovine bone BMP is functional when surgical repair products derived from bovine sources are used in humans.

A variety of methods and compositions of biomaterials have been used to repair or regenerate bone loss due to either trauma or disease. Conventional implantable bone repair materials provided a matrix or scaffolding for migration into, proliferation and subsequent differentiation of cells responsible for osteogenesis (Nashef U.S. Pat. No. 4,678,470). While the compositions provided by this approach provided a stable structure for invasive bone growth, they did not promote bone cell proliferation or bone regeneration. Generally, these materials are referred to as osteoconductive.

Subsequent approaches have used bone repair matrices containing bioactive proteins which when implanted into a bone defect provided not only a scaffolding for invasive bone ingrowth, but active induction of bone cell replication and differentiation. These materials are generally referred to as osteoinductive.

In general, osteoinductive compositions comprise a matrix which provides the scaffolding for invasive growth of the bone, anchorage dependent cells, and an osteoinductive protein source. The matrix may be a variety of materials, such as: collagen (Jefferies U.S. Pat. Nos. 4,394,370 and 4,472,840); inorganically based materials, such as a biodegradable porous ceramic (Urist U.S. Pat. No. 4,596,574); or, polylactic acid (Urist U.S. Pat. No. 4,563,489).

Osteogenic compositions and methods for making the same are described in Jefferies U.S. Pat. Nos. 4,394,370 and 4,472,840. Jefferies describes complexes of reconstituted collagen and demineralized bone particles or complexes of reconstituted collagen and a solubilized bone morphogenetic protein, fabricated into a sponge suitable for in vivo implantation into osseus defects. Structural durability of these compositions may be enhanced by crosslinking with glutaraldehyde.

In particular, two specific substances have a well established ability to induce the formation of new bone (i.e., to be osteoinductive) through the process of osteogenesis: demineralized bone particles or powder, and bone morphogenetic proteins (BMPs) (Urist U.S. Pat. Nos. 4,595,574, 4,563,489, 4,551,256). A variety of other bone inducing factors have been characterized and claimed for various uses (Seyedin et al., U.S. Pat. Nos. 4,627,982; 4,774,228; 4,774,322; 4,810, 691 (RE34090); and 4,843,063 (RE35694)).

Bone derivatives and bone products have been disclosed as useful for other than implant or surgical applications. U.S. Pat. No. 6,344,437 describes method of enhancing bone strength by orally administering a composition of degraded collagen, calcium and vitamin $D_3$ (Claims 1, and 2 and 3). Demineralized bone protein fraction (fraction D, Reference Example 4) was not used for any orally administerable composition. Furthermore, the patent teaches that calcium is to be used in combination with the bone derivative.

U.S. Pat. No. 4,427,583 discloses a countercurrent flow process for demineralizing animal bone in order to prepare an edible ossein protein product. The patent discloses various chemical processing steps for obtaining a demineralized bone product but there is no disclosure of any edible uses or effects.

Romanian Patent 90,405 (Oct. 30, 1986) discloses a "biostimulating and remineralizing product" for use in the treatment of "demineralizing organic conditions." (See translation, page 1.) The product composition includes "protein depleted bone minerals" (See page 2) obtained from "total cattle bone powder." The total cattle bone powder and protein depleted minerals are mixed with ingredients to provide "a pleasant sweet taste" and further includes royal jelly, dried rose hip jam, honey, and tamarisk jam in order to produce an edible composition. Additionally, it is noted that the product specifically includes "1.5 parts sodium fluoride," which is equal to about 1.5 wt % based on the formulation disclosed (See page 2).

SUMMARY OF THE INVENTION

Nutritional supplements and methods for maintaining and/or improving the condition of bones and cartilage in a mammal, particularly a human. One such supplement comprises demineralized bone matrix (DBM) wherein the DBM comprises a bone growth improving amount of osteoinductive growth factor (OGF). A preferred supplement composition further comprises at least one vitamin, such as vitamin E. One method comprises orally administering to the mammal on a periodic basis a supplement comprising DBM. In a preferred method the DBM composition is periodically administered and there is a further periodic administration of a therapeutically effective amount of a calcium-containing composition; the calcium-containing composition is administered temporally spaced apart from said DBM composition for maximum effectiveness.

DETAILED DESCRIPTION

For purposes of the present invention and to aid in understanding various terms and phrases, in addition to those above, are defined as follows:

Antioxidant: a natural or synthetic substance typically added to a composition to inhibit, reduce or delay deterioration or oxidation of the composition, or one or more active components in the composition, due to the action of oxygen in the air or dispersed or dissolved in the composition. Also see "preservative."

Bone: bone recovered from any source including animal and human. Such bone includes any bone or portion thereof, including cut pieces of bone, including cortical and/or cancellous bone, for example, recovered from a human or animal. Such bones include for example, the humorous, hemi-pelvi, tibia, fibula, radius, ulna, rib, vertebrae, mandibular, femur, and, ilia, and any cut portion thereof, and also including continuous or discontinuous bone portions. When referred to generally, such bone includes demineralized and not demineralized bone. In a preferred embodiment cancellous or cortical bone material is demineralized. For purposes of the present invention all such forms of bone include one or more therapeutically beneficial substances including, for example, at least one of bone morphogenetic protein and/or transforming growth factor-$\beta$.

Bone Morphogenetic Protein (BMP): BMP comprises a family of proteins and has been designated or identified as BMP-1 through BMP-8, inclusive, as disclosed in U.S. Pat. No. 4,877,864; U.S. Pat. No. 5,013,649; WO 90/11366; and WO 91/18098, as well as BMP-9, BMP-10, BMP-11, BMP-12 and BMP-13. These substances are further described and disclosed hereinbelow. Such proteins can be extracted from demineralized bone matrix (DBM) by methods known in the art and used apart from the demineralized bone. A preferred BMP is BMP-2, the mature protein sequence beginning with the amino acid Gln at nucleotide 1202 and ending with the amino acid Arg at nucleotide 1543, as described in detail in U.S. Pat. No. 5,013,649. Combinations of two or more of such osteogenic proteins are suitable for use in the present invention, as are fragments and heterodimeric forms of such proteins that exhibit osteogenic activity.

Demineralized Bone: one or more distinct bone portions which have been demineralized by any method well known to those of ordinary skill in the art. Typically, cortical and cancellous bone are demineralized in hydrochloric acid for a period of time of about 15 minutes to about 8 hours or more at temperatures ranging from less than ambient, e.g., greater than about 0° C. to about 22° C. to temperatures slightly to moderately elevated above ambient, e.g., about 25° C. to about 50° C. Typically, cortical and/or cancellous bone is demineralized to contain less than about 10 wt % residual calcium; preferably about less than about 5 wt % residual calcium; more preferably about 1 wt % to about 3 wt % calcium; even more preferably about 2 wt % residual calcium or less; for example, containing trace amounts to about 2 wt %. Other methods for demineralizing bone are well known in the art to which the present invention pertains, and can be readily selected and employed by one of ordinary skill in the art, without undue experimentation. Further detailed descriptions of suitable methods are set forth below. When bone is suitably demineralized and in particulate form the resulting material can also be referred to as demineralized bone matrix (DBM) or demineralized bone powder. A DBM suitable for use in the present invention comprises substances such as bone morphogenetic protein (BMP) described above, collagen type I and at least one chondroblast or osteoblast stimulating growth factor. It is known that the major collagen of skin, tendon, and bone is the same protein containing two alpha-1 polypeptide chains and one alpha-2 chain. Osteoblast stimulating growth factor is also referred to as insulin-like growth factor I or IGF-I; it is known to induce various cellular activities, including bone growth. A chondroblast is a cell that arises from the mesenchyma and forms cartilage. Osteoblast stimulating growth factor comprises at least one substance selected from the group consisting of transforming growth factors-beta (TGF-$\beta$), such as TGF-$\beta$1 and TGF-$\beta$2, BMP-2 through BMP-13, inclusive, insulin-like growth factor (IGF), including IGF-I and IGF-II, platelet-derived growth factor (PDGF), including PDGF AA, PDGF BB and PDGF AB, and fibroblast growth factors (FGF), particularly basic-FGF or FGF2. The osteoblast stimulating characteristics of a substance can be characterized, for example, by observation of increased proliferation of an osteoblastic cell line in culture, including a cell line selected from the group consisting of MC3T3-E1, AsOS2, TE85 and MG63. Alternatively, osteoblast stimulation can be measured by an altered expression of osteoblastic markers, e.g., alkaline phosphatase, osteocalcin and osteopontin. Chondroblastic stimulation can be measured by increased rate of proliferation of a cultured chondroblastic cell line, such as in a cell line selected from the group consisting of HTB-94, TMC23, and ATDC5. Alternatively, chondroblast stimulation can be measured by altered expression of a chondroblastic marker such as collagen II, collagen X or hyaluronic acid, in cultured chondrocytic cells.

Collagen: the protein substance of the white fibers (collagenous fibers) of skin, tendon, bone, cartilage and all other connective tissue, composed of molecules of tropocollagen, it is converted into gelatin by boiling. The term collagenous pertains to collagen, forming or producing collagen. Collagen is distinguished from bone by those skilled in the art, particularly relating to bone and collagen derived compositions useful for bone repair. For example, U.S. Pat. No. 4,440,750 discloses a two component composition that is used for bone repair or construction, "(p)articulate demineralized bone and reconstituted collagen are the two principal components of the composition." (col. 1, lns. 63-65)

Comprise or comprising: throughout the entire specification, including the claims, the word "comprise" and variations of the word, such as "comprising" and "comprises," as well as "have," "having," "includes," "include" and "including," and variations thereof, means that the named steps, elements or materials to which it refers are essential, but other steps, elements or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps.

Consisting essentially of: in the present context, "consisting essentially of" is meant to exclude any element or combination of elements as well as any amount of any element or combination of elements that would alter the basic and novel characteristics of the invention. Thus, by way of example, a DBM composition that is modified so as to inactivate the bone growth promoting component(s) present would be excluded.

Mammal: for purposes of the present invention mammal refers to any animal classified as a mammal, including humans, domestic and farm animals, and zoo, sports, or pet animals, such as dogs, horses, cats, cows, etc. Preferably, the mammal is human.

Osseous tissue: also referred to as bone tissue. It is a connective tissue, the matrix of which consists of collagen fibres and ground substance and in which are deposited calcium salts (phosphate, carbonate, and some fluoride) in the form of an apatite mineral. Prior to calcification, osseous tissue is referred to as osteoid tissue. It is uncalcified bone matrix that is produced in the body by osteoblasts. It consists mainly of collagen, but has osteonectin present.

Osteoconductivity (or osteoconductive): the ability of a substance to serve as a scaffold for bone growth. Osteoconductive materials are typically biocompatible matrix materials, for example, hydroxyapitate; collagen; biocompatible matrix materials including for example, polymeric matrix materials, bioglass, bioceramics, resorbable biomaterials, bioabsorbable polymers, a plastic matrix, stainless steel, titanium, and cobalt-chromium-molybdenum alloy matrix; and commercially available, synthetically prepared substances that include hydroxyapitate.

Osteogenic: commonly refers to bone formation by living cells.

Osteoinductivity (or osteoinductive): the ability of a substance to induce osteoblast differentiation for the promotion of bone growth. Osteoinductive substances include but are not limited to, for example, autograft bone; allograft bone; commercially available synthetic grafting compositions; demineralized cortical bone, demineralized cancellous bone and collagen, and mixtures thereof. For suitable use in the present invention, such substances comprise or include one or more growth factors, specifically, osteoinductive growth factors. Such growth factors include for example, bone morphogenetic protein (BMP) and transforming growth factor-beta (TGF-β, see below). Osteoinductive substances can be characterized, for example, by their ability to alter the expression of markers associated with osteoblasts, chondroblasts, osteocytes, or chondrocytes in cultured cells. Such markers include, for example, with regard to osteoblast stimulation, alkaline phosphatase, osteocalcin, osteopontin; and with regard to chondroblast stimulation, collagen II, collagen X, and hyaluronic acid in cultured chondrocytic cells. As described in further detail in the present disclosure, a demineralized bone product useful in the present invention is typically demineralized to the extent that it comprises less than about 6 wt % residual calcium; preferably comprising about 1 wt % to about 3 wt % residual calcium; more preferably comprising about 2 wt % residual calcium or less; for example, comprising trace amounts to about 2 wt %.

Pharmaceutically acceptable carriers, excipients or stabilizers: typically such compounds, compositions or mixtures as those described in Remington's Pharmaceutical Sciences 16th edition, Osol, A. Ed. (1980) that may be included in the composition provided that such materials do not adversely affect the desired characteristics of the composition. Acceptable carriers, excipients or stabilizers are nontoxic to recipients at the dosages and concentrations employed and include; additional buffering agents; preservatives; antioxidants; biodegradable polymers; compounds useful for preparing a dosage form, including tablets and capsules; and mixtures thereof.

Preservatives: compounds that can be used to substantially inhibit or prevent undesirable changes to substances, compounds or compositions either by direct chemical reaction or that are added in order to destroy, prevent, or inhibit the proliferation of microorganisms, e.g., bacteria, yeast and mold, during manufacturing, storage and/or use of the nutritional composition. Examples of potentially useful preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, phenyl ethyl alcohol; phenoxyethanol; benzoic acid; lower alkyl esters of para-hydroxybenzoates, referred to as parabens, including alkyl parabens such as methylparaben; ethylparaben; propylparaben; butylparaben; catechol, resorcinol, cyclohexanol, 3-pentanol, m-cresol. Preservatives can be used individually and in combination with one another; combination products are also commercially available. One or more antimicrobial preservatives can optionally be included in the composition in an amount of about 0.001 to about 10 weight percent, preferably about 0.05 to about 2 weight percent.

Protein: a sequence of amino acids for which the chain length is sufficient to produce the higher levels of tertiary and/or quaternary structure. This is to distinguish from "peptides" or other low molecular weight compounds that do not have such structure. Typically, the protein will have a molecular weight of at least about 15-20 kD, preferably at least about 20 kD. Examples of proteins encompassed within the definition herein include mammalian proteins, such as, e.g., osteoinductive factors; bone morphogenetic proteins (BMP); and biologically active fragments or variants of any of the proteins.

Substantially: for purposes of the present invention, unless otherwise defined with respect to a specific property, characteristic or variable, the term "substantially" as applied to any criteria, such as a property, characteristic or variable, means to meet the stated criteria in such measure that one skilled in the art would understand that the benefit to be achieved, or the condition or property value desired is met.

TGF-beta: Transforming Growth Factors-β (TGF-β) refers to multifunctional peptides that control proliferation, differentiation and other functions in many cell types, including bone. It is reportedly a potent stimulator of osteoblastic bone formation. TGF-β is the prototype of a protein family also known as the TGF-β superfamily. The family includes inhibin A and B, activin-A, B and AB, Mullerian inhibiting substance, bone morphogenetic proteins, decapentaplegic and vegetalising factor-1. The TGF-β superfamily may comprise as many as 100 distinct proteins. TGF-β exists in at least five isoforms known as TGF-β-1 through TGF-β-5 inclusive; TGF-β-1 is the prevalent form. Mature human, porcine, simian, chicken and bovine TGF-β-1 are identical.

Therapeutically effective, or beneficial, amount: the amount of a therapeutically beneficial substance or mixture of substances, including specifically, DBM and a combination of DBM with at least one nutritional supplement, such as a vitamin, mineral, etc., that provides a therapeutic benefit in the management of a bone-related condition or bone health. It should be understood by one of ordinary skill in the art that a therapeutically effective, or beneficial, amount can vary depending on the condition involved, the severity and course of the condition, whether the nutritional supplement is administered for maintenance, prevention or therapeutic purposes, previous therapy, the particular individual and that individual's history and response to the supplement, the composition and concentration used, and the discretion of the attending professional. The composition is typically suitably administered to an individual over a period of time in a series of treatments. The composition(s) may be administered in the forms described herein or in conjunction with other compositions or therapies useful in treating the condition in question. Such an amount can be readily determinable by a person of ordinary skill in the art, including pharmacists, medical professionals, veterinarians, etc.

Therapeutically beneficial: any material which by its action or presence, bring about a therapeutic result in an individual. Such materials include but are not limited to, for example, one or more of the following: osteoinductive substances, osteoconductive substances, and nutritionally active agents. Such therapeutically beneficial substances may optionally be provided with a carrier. Suitable osteoinductive substances include but are not limited to, for example, demineralized cortical bone and demineralized cancellous bone, and mixtures thereof, each including one or more growth factors; growth factors including for example bone morphogenetic protein, and transforming growth factor-β. Suitable osteoconductive substances include but are not limited to, for example, hydroxyapitate; collagen; any biocompatible matrix material including for example, polymeric matrix materials, bioglass, bioceramics, resorbable biomaterials; bioabsorbable polymers; a plastic matrix; stainless steel; titanium; cobalt-chromium-molybdenum alloy matrix; and substances including hydroxyapitate. Suitable nutritionally active agents include but are not limited to, for example, growth factors including for example bone growth factors including for example bone morphogenetic protein, and transforming growth factor-β; vitamins; minerals; chemotherapeutic agents; anti-inflammatory agents; antibiotics; antioxidants; stabilizers; and preservatives.

Demineralized bone matrix (DBM) is a well-known and commercially available material. Various mammalian sources of bone are suitable for producing DBM although, as a practical matter, it is convenient to use bovine or porcine sources. In particular, the source of the bone for preparation of the DBM need not be of the same specific species as the mammal that will use the resulting nutritional composition. Various methods have been described in the literature for its preparation. In each instance, however, DBM useful in the present invention is preferably lyophilized to produce the powder for use as a nutritional supplement. An optional treatment step includes dispersing the DBM in a substantially saturated sodium chloride, salt, solution at about 50° C. to about 55° C. for about 12 to about 24 hours in order to further facilitate the breakdown of collagen in order to make the beneficial components of DBM more readily accessible. If this step is used, the DBM is recovered from the salt solution by filtration and washing and it is then lyophilized as stated above. Useful DBM typically has particle sizes of about 10 μm to about 1000 μm; preferably about 50 μm to about 500 μm; more preferably about 75 μm to about 300 μm; for example about 100 μm to about 200 μm; such as about 100 μm, although smaller or larger particle sizes are also useful.

As an example of the preparation of demineralized bone matrix U.S. Pat. No. 4,394,370 provides a useful detailed method for the preparation of demineralized bone particles: Allogenic bone material was obtained from human cadavers from an organ bank, although, as discussed herein, for purposes of the present invention, alternative sources of suitable bone are available. Bones were cleaned and extracted with absolute ethanol followed by anhydrous ethyl ether. The bones were then pulverized in a liquid nitrogen impacting mill (Spex Industries, Metuchen, N.J.) and sieved to particle size of less than 75 millimicrons to yield bone powder particles.

Demineralized bone powder, DBP (referred to herein as demineralized bone matrix, DBM) was prepared by extracting the previously prepared bone powder particles with 0.5 M HCl (25 Meq/gm bone) for 3 hours at room temperature followed by six washes in sterile distilled water to remove all acids and calcium, followed by four sequential 60-minute washes in absolute ethanol and anhydrous ether.

Alternatively, U.S. Pat. No. 4,440,750 describes a similar process for preparing demineralized bone matrix generally as follows: "The bone that is used in the invention (as well as herein) may also typically be collected from a variety of mammalian sources. Homogeneic and xenogeneic sources may be used. Bovine and porcine bone, preferably long bone, will normally be used because of its availability. The surface of the bone is first cleaned by physically removing periosteum by scraping or brushing. The bone is then fragmented into small pieces and the fragments are water washed with agitation to remove any water soluble materials remaining on the fragments. The washing is preferably carried out at reduced temperatures, usually about 5° C. to about 18° C., with frequent changing of the wash water. The fragments are then dried, extracted with one or more lipophilic solvents, such as ethanol and ethyl acetate, to remove lipids and dehydrate the bone. The fragments are then dried under vacuum and comminuted by crushing, milling or pulverizing, preferably at reduced temperatures to increase the friability of the bone. The bone is accordingly converted into a finely divided powder having a particle size in the range of about 25 to 1000 microns, preferably 75 to 250 microns. Division of the bone into small particles facilitates; extracting the minerals from it and increases the volume fraction of induced bone formation." (Col. 3, lns. 5-28)

The principal mineral component of bone is calcium phosphate. The term calcium phosphate as used herein is intended to encompass the numerous calcium-phosphorus complexes and compounds present in bone such as the various polycalcium phosphates, hydroxyapatite, chlorapatite, and the like. Calcium phosphate usually constitutes about 80% of the mineral content of bone. Other mineral components of bone include calcium carbonate, calcium fluoride, calcium chloride, and magnesium phosphate. These minerals are normally soluble in dilute mineral and organic acids and such acids may be used to demineralize bone. The concentration of the acid used to demineralize the bone will typically be about 0.05 N to about 2.0 N. Hydrochloric acid is preferred and it is preferably used at a concentration of about 0.6 N. The bone will normally be cut, crushed, ground and/or comminuted to a desired particle size, typically about 1 micron to about 2000 microns; preferably about 100 microns to about 500 microns. The particulate bone is then contacted with the acid for about less than one hour to several hours, overnight or even over several days at temperatures ranging from about greater than about 0° C. to temperatures moderately elevated above room temperature, e.g., about 3° C. to about 50° C.; for example about 5° C. to about 30° C. Agitation can facilitate extraction of the minerals from the bone. Agitation can include equipment for mechanical agitation as well as ultrasonic equipment. After the extraction step is completed the bone is separated from the acid such as by sedimentation, filtration or other conventional solid-liquid separation techniques, and the bone is washed in various steps with water, ethanol, and/or ether to remove residual tissue as well as adsorbed or absorbed acid and initially to dehydrate it. The thus treated bone is further dried and preferably lyophilized and may be sterilized by irradiation, ethylene oxide treatment, or other known solids sterilization methods.

A specific preparation of demineralized bone powder is described in U.S. Pat. No. 4,440,750 as follows:

"Fresh bovine femur is brushed to remove periosteum and then fragmented into pieces less than 0.5 cm largest dimension. The fragments are washed in water at 5° C. with agitation for one day with frequent change of the wash water. The fragments are then extracted at room temperature three times with 95% ethanol for 20 minutes each time. The volume of ethanol in each extraction is triple the volume of bone. The fragments are then dried under vacuum at ambient temperature and then extracted three times with ethyl acetate. Each extraction is made for 20 min. The ethyl acetate volume is triple the bone volume. The fragments are again dried under vacuum and are then pulverized in a liquid nitrogen mill. The pulverized powder is sieved and the 75-450 micron portion is recovered. That portion is extracted with 0.5 N HCl at room temperature for three hours. The volume of HCl is ten fold the bone volume. Following the HCl extraction the pulverized bone is washed until the pH of the wash liquid reached 5. The triple ethanol and ethyl acetate extractions are then repeated." (Col. 5, lns. 11-31)

More recently, an alternative method has been reported for demineralizing bone using 0.6 N HCl heated to 60° C. in a controlled heat ultrasonic cleaner for about 20 minutes. The treated bone is washed with sterilized, distilled water and given a further short treatment with 30% hydrogen peroxide, followed by dehydration with alcohol. (See, "A Simplified But Effective Demineralizing Method for Osteogenic Allograft Preparation," H. I. Shin, et al., Key Engineering Materials, Vols. 288-289 (2005), 249-252.)

Typically, the amount of lyophilized DBM useful for administration to a human on a daily basis is about 10 mg to about 10 g; preferably about 20 mg to about 1 g; more preferably about 50 mg to about 600 mg; for example about 175 mg to about 500 mg; such as about 150 mg, about 200 mg or about 300 mg. The amount can be adjusted depending on whether the administration is for maintenance of a healthy bone health condition, in anticipation of decreased bone health or whether or not the individual is exhibiting signs of decreased bone health. A skilled professional nutritionist or medical professional is capable of adjusting the amounts as needed.

DBM useful in the present invention contains bone-active substances, e.g. osteogenic proteins, that are active for the formation of osseous tissue. Osteogenic proteins useful in the present invention are well known to those skilled in the art and include those of the bone morphogenetic protein (BMP) family identified as BMP-1 through BMP-8, inclusive, as disclosed in U.S. Pat. No. 4,877,864; U.S. Pat. No. 5,013,649; WO 90/11366; and WO 91/18098, as well as BMP-9, BMP-10, BMP-11, BMP-12 and BMP-13. Such proteins can be extracted from DBM by methods known in the art and used apart from the demineralized bone. Preferred is BMP-2, the mature protein sequence beginning with the amino acid Gln at nucleotide 1202 and ending with the amino acid Arg at nucleotide 1543, as described in detail in the '649 patent identified above. Combinations of two or more of such osteogenic proteins may be used, as may fragments and heterodimeric forms of such proteins that exhibit osteogenic activity. Furthermore, such protein can be native or recombinant protein.

The activity of the bone-active element(s) in the DBM useful in the present invention can be determined using standard assay tests well known in the art. Such tests can also be used to check the stability and activity of compositions after storage. One assay for chondrogenic activity (the ability to produce chondrocytes or cartilage cells) is described in U.S. Pat. No. 4,627,982, incorporated herein by reference. The procedure is described as follows (col. 5, ln. 29 to col. 8, ln. 2):

The presence of the desired proteins can be confirmed using an in vitro assay for the production of proteoglycans (PG), the identity of which is confirmed by enzyme-linked immunosorbent assay (ELISA). The assay is an agarose gel culture model using leg muscle cells isolated from rat fetuses. It assesses the ability of the DBM samples to induce the production of cartilage specific PGs. The correlation between in vitro cartilage induction and in vivo bone formation has been shown by Seyedin, S., et al, J Cell Biol (1983) 97: 1950-1953. Additionally, activity of the DBM can also be determined by assessing the ability of the protein to induce the formation of cartilage, chondrocyte, chondroblast, bone, calcified bone, osteoblasts, and/or osteocysts in a heterotopic site, such as a rat or mouse muscle. (Urist, 1965 supra)

In a preferred method a cell culture is prepared by removing muscle tissue aseptically from the upper limbs of nineteen-day-old Sprague Dawley rat fetuses, mincing the tissue, and culturing it in Eagle's Minimum Essential Medium (MEM) with 10% fetal bovine serum (FBS) and 50 units penicillin, 50 micrograms streptomycin per ml. Cellular outgrowth usually reaches confluency within one week, whereupon cells are trypsinized, split 1:2 and used for experimentation within the first three passages.

The cells are placed in agarose gel cultures either with control medium or with samples to be tested. The procedure is basically that of Benya, et al, Cell (1982) 30: 215. Briefly, the cell monolayers are harvested by trypsinization, counted on a hemocytometer, and resuspended at two times the final cell concentration in the medium with or without the protein fraction to be tested. The control medium is either Hams F12, Dulbecco's Minimum Essential Medium (DMEM) or CMRL 1066 (Gibco) each containing 10% FBS and antibiotics. The test protein fractions in 0.01N HCl are diluted directly to the desired concentration of test protein diluted with an equal volume with 1% low melting agarose (Bio-Rad, #162-0017) in F-12, and 0.2 ml of the dilution is plated on 17 mm wells coated with 0.15 ml of 1% high melting (Bio-Rad, 190 162-0100) agarose. The resulting cultures are incubated at 37° C. for 5 min, chilled at 4° C. for 10 min, and then overlayed with 1 ml of the corresponding medium (control or test protein). The cells are then cultured in a humidified atmosphere of 5% $CO_2$, 95% air and fed every 3-4 days thereafter by a complete change with control medium. After 7 days the cultures are frozen and stored at −80° C. before assay.

The cultures are assayed by thawing at 4° C., homogenizing in 4M guanidine-HCl with 50 mM Na acetate, 13 mM EDTA, 6 mM NEM, and 3 mM PMSF at pH 5.8, and extracting by shaking overnight at 4° C. The supernatant fraction from centrifugation at 25,000×g for 40 min at 4° C. is dialyzed overnight at 4° C. against 50 volumes 0.2M NaCl, 50 mM Tris, pH 7.4. The supernatant is assayed for proteoglycans by ELISA as described by Renard, et al, Anal Biochem (1980) 104: 205, and in U.S. Pat. No. 4,434,094.

Briefly, for the ELISA, antiserum to cartilage PGs was raised in rabbits using standard techniques which showed no cross-reactivity with hyaluronic acid or PGs extracted from rat bone. Purified proteoglycn (Seyedin, S., et al., spura) from Swarm rat chondrosarcoma tissue is used as standard antigen. The dialyzed samples are diluted 1:1 (v/v) in phosphate-buffered saline (PBS) with 0.05% Tween 20, 1 mg/ml bovine serum albumin (BSA), pH 7.2 for assay. Horseradish peroxidase conjugated goat anti-rabbit IgG (Tago) is the second antibody with o-phenylenediamine as substrate.

Bioassay System: Osteoinductive ability of samples is assayed by their ability to induce endochondral bone formation intramuscularly in athymic rats. The samples are wetted with two volumes of sterile double distilled water (v/w), thoroughly mixed, packed in a 1 cc syringe, cut and weighed. Samples are implanted on the ventral thoracic region, one on each side of the animal. Explants were removed after 14 and 28 days and evaluated biochemically and histologically.

Histologic Evaluation: Explants removed after 14 and 28 days are subjected to histological assessment by fixing in 10% neutral formalin for 26 hr, and then processing for paraffin embedding. Four-six micron sections are taken from the imbedded tissues and are subsequently stained with either hematoxylin-eosin (general cytology), with safronin-O (proteoglycans) and Gomori trichrome (collagen).

Biochemical Assays: The 14 day explants are split in half, the wet weight determined and frozen at −80° C. until processed. The samples are first extracted and assayed for alkaline phosphatase activity and subsequently extracted and assayed for cartilage-specific proteoglycans. The right side 28 day explants are extracted and assayed first for alkaline phosphatase and then for calcium. The extraction and assay procedures are described below.

Proteoglycan Assay: Cartilage proteoglycan is assayed by an ELISA technique. The explants are weighed immediately after removal and frozen at −70° C. until extraction. For the extraction, the explants are cut into slices, and homogenized in ice cold extraction buffer in a Tekmar Tissuemizer for two 30 sec bursts at maximum setting. The extraction buffer is 6M guanidine hydrochloride, 75 mM sodium acetate or 4M guanidine hydrochloride, 50 mM acetate both containing 20 mM EDTA, 1 mM PMSF and 10 mM NEM at pH 5.8. Buffer is used in a 10:1 volume to the weight of the explant extracted, and the samples are incubated overnight (20 hr) at 4° C. The samples are then centrifuged at 12,000 rpm for 1 hr at 4° C., and the supernatants dialyzed overnight at 4° C. against 50 volumes of 50 mM Tris, 200 mM NaCl, pH 7.4. The dialyzate is subjected to ELISA performed as described by Renard, et al, Arch Biochem Biophys (1980) 207: 399 and by Seyedin, S., et al, J Cell Biol (1983) 97: 1950 using polystyrene microplates (Flow Laboratories, McClean, Va.). The antisera and the proteoglycan standard are prepared from Swarm rat chondrosarcoma tissue as described by Seyedin, S., et al, (supra). Horseradish peroxidase conjugated goat anti-rabbit IgG is used as the second antibody, samples are assayed in different solutions in PBS, 0.05% Tween 20, 1 mg/ml BSA and quantitated by use of the inhibition ELISA described by Shuures, et al, Clin Chim (1977) 81:1.

Extractable Calcium: The formation of bone is also assessed by determination of calcium. The explants are cut into small pieces and suspended in 1:10 (m/v) of 0.5N HCl to dissolve the ions. The samples are incubated for another 5 days at room temperature and centrifuged at 12,000 rpm for 40 min. The calcium concentration of the supernatant is determined by atomic adsorption (Trace Analysis Laboratory, Hayward, Calif.).

Analysis for Alkaline Phosphatase: To determine alkaline phosphatase (AP), the explants are cut into small pieces and homogenized in 10 volumes (1/10) of ice cold 1.5M NaCl, 3 mM $NaHCO_3$, pH 7.5. The homogenized samples were then centrifuged at 12,000 rpm for 50 min at 4° C., and an aliquot of the supernatant diluted 1:10 in cold distilled water. The method of Huggins, et al, J Exp Med (1961) 114: 761 is used to assess alkaline phosphatase using polystyrene plates.

In addition to providing the compositions disclosed herein, the invention also includes a method for administering the composition of the invention to a mammal, particularly an individual who has or is at risk of having bone-related deficiencies or desires to maintain bone health. Typical effective doses are 1 to about 6; alternatively 1 to about 5; 1 to about 4; 1 to about 3; 1 to about 2; most preferably 1 dose per day. More particularly, the invention includes a method for orally administering at least the DBM-containing composition of the invention to an individual who has, is at risk of, or may be at risk of bone-related deficiencies or conditions. The compositions of the present invention are particularly useful in people having one or more major and/or minor risk factors for bone-related conditions, including for example, risk factors for osteoporosis, other diseases or conditions that affect the health or conditions of the bones and advancing age. The compositions are preferably administered orally but if the active component(s) present in the DBM (for example, the osteoinductive factors) are used in the substantial absence of the bone matrix, administration may be parenteral, sublingual, intranasal, transdermal, or buccal, including such forms as nasal sprays, aerosols, suppositories, and transdermal patches. Suitable forms for the DBM- and calcium-containing compositions include tablets, capsules, caplets, lozenges (including fast melt forms), syrups, granules, solutions, and suspensions which contain unit dose(s) of the composition for administration once, several times a day, or weekly. The composition of the invention will typically be administered orally as a tablet, caplet, or a capsule. A single dose of the DBM-containing composition in tablet, caplet, or capsule form can be one, two, three, four, five, six or more tablets, caplets or capsules. It is preferred to have a single dose in two tablets, caplets, or capsules including one each of the DBM-containing composition and the calcium-containing composition. Dosage forms of the invention such as tablets, caplets, gel tabs, capsules, liquid and sustained release formulations, and the like can be formulated and prepared according to manufacturing techniques well known in the pharmaceutical industry.

All of the amounts and ranges of ingredients of the compositions of the invention given herein are on a per dose basis. A single dose of a DBM-containing composition is typically suitable for the daily requirements of individuals, although in some situations multiple doses per day are indicated. Most preferably, the dose of DBM is contained in one, two or three dosage units. Additionally, the preferred administration method of the nutritional supplement includes administration of a calcium-containing composition. The calcium-containing composition can be given concurrently with the DBM-containing composition or sequentially. Sequential administration of the DBM and calcium containing compositions is preferred with the calcium-containing composition to be given following the DBM-containing composition. Without wishing to be bound by theory, while it is believed that a calcium supplement is beneficial for bone health, if calcium is present with the active component(s) in DBM then bone formation may not occur as readily, to the same extent or at the same rate.

When administered in conjunction with administration of the DBM-containing composition, the amount of calcium usefully administered is typically about 40 mg to about 2000 mg; preferably about 50 mg to about 1200 mg; more preferably about 60 mg to about 800 mg.

In any event, for purposes of the present invention it is preferred that the calcium-containing composition be administered subsequent to the DBM-containing composition. In order to facilitate their sequential absorption by the body, the sequence of administration should take into account the normal gastric cycles in the mammal to which the compositions are being administered; such cycles can vary by species, but are generally known to those skilled in the art.

In the case of human beings, such digestive processes have been studied extensively in connection with the controlled release of drugs. Controlled release dosage forms that provide for prolonged delivery of active agent formulations to the environment of use have found application for increasing numbers of active agents. However, with respect to pharmaceutical and veterinary active agent formulations, there has been a need not only to provide for prolonged delivery of the active agent over time, but also to provide prolonged delivery of the active agent at a particular location or locations in the environment of use, such as in the stomach or in the intestines.

Certain active agents are absorbed primarily from the small intestine whereas others are absorbed in the digestive tract. Generally, the time of passage of different particle sizes through the small intestine does not vary significantly, and passage is generally independent of food intake and particle size. Thus, an active agent dissolved in liquid, solid active agent dispersed in liquid and relatively larger delivery units of active agent, such as microcapsules and the like, will traverse the length of the small intestine in substantially the same time frame, usually about 3 to about 5 hours. For active agents that are not easily absorbed by the small intestine or that do not dissolve readily, the window for active agent absorption in the small intestine may be too short to provide a desired therapeutic effect. This fact often creates a need for frequent dosing of active agent in order to provide and maintain adequate levels of active agent in blood plasma. The need for frequent dosing presents compliance problems and is often inconvenient for the user as well.

Since it has been found difficult to alter the transit time of active agent through the small intestine, some emphasis has been placed on attempting to control the transit time of active agents in the stomach. Most active agents are not well absorbed in the stomach, but even in those instances where the active agent is not well absorbed, the continuous release of active agent in the stomach over a prolonged time period will dispense active agent over that same period of time to the small intestine where it can be absorbed.

The physiological behavior of the stomach is usually determined by whether it contains food or is empty. Food is mixed and partially digested in the distal stomach (antrum). As the stomach undergoes contractions, partially digested material is discharged into the small intestine and undigested material is retropelled into the main part of the stomach for further digestion. In the fed state, undigested material is not generally able to leave the stomach. At the end of a digestive period, the stomach enters the fasting stage and begins a cycle called the interdigestive myoelectric motor cycle or IMMC.

The IMMC can be considered to be divided into four phases: (1) phase 1 is an approximately one hour period with no contractions; (2) phase 2 is about a forty minute period of intermittent potentials and contractions that increase in intensity over time; (3) phase 3 is a relatively short period, generally between about five to about fifteen minutes, of intense contractions (commonly called the "housekeeper wave") that completely empties the stomach; and (4) phase 4 is a short transitory period between the intense activity of phase 3 and the quiescence of phase 1. The different phases move distally from the stomach to the terminal ileum over an approximately two hour period as the cycle is repeated. Since the cycle is interrupted by the receipt of food by the stomach, it is possible to delay the emptying phase, phase 3, by maintaining a fed state. However, it is not practical to regularly maintain the fed state over a long period of time. Consequently, where it is desirable to have an active agent remain in the stomach, a need exists for a delivery device that can remain in the stomach for a significant period, whether in the fed or fasted state, and deliver the active agent to the stomach over a prolonged period of time.

Significant effort has been expended to develop controlled release dosage devices and formulations in order to achieve controlled delivery. Such technology can be relevant to the present invention where it is desired to controllably separate the active component(s) present in DBM from a calcium-containing composition in order to maximize the beneficial effect of the active component(s) in DBM. Alternatively, one method would be to administer the DBM-containing composition at a higher dosage level and in combination with a calcium-containing composition or to administer the DBM-containing composition in the substantial absence of administration of a calcium-containing composition. Where both compositions are administered, such administrations are preferably spaced apart in time, or temporally spaced apart. Preferably, the DBM-containing composition is administered first, followed by administration of the calcium-containing composition. In view of the above knowledge relating to gastric cycles in humans, typically the compositions are administered about 1 to about 4 hours apart; preferably about 1.25 to about 3.75 hours apart; more preferably about 1.5 to about 3 hours apart; for example, about 1.75 to about 2.75 hours apart. If the gastric emptying cycle is interrupted by the additional ingestion of food, the time interval before administration of the calcium containing composition should be extended in order to allow for the DBM-containing composition to be absorbed in the stomach or to pass into the intestines for absorption. Furthermore, for convenience, it is also possible to administer the DBM-containing composition and the calcium-containing composition on different days so that interference cannot occur. Alternatively, the calcium-containing composition can be administered for one or more days followed by administration of the DBM-containing composition temporally spaced apart from the last administration of the calcium-containing composition, including on the next day, if convenient. Conversely, the DBM-containing composition can be given for one or several days followed by administration of the calcium-containing composition temporally spaced apart on the same or next day. Additionally, where the compositions of the present invention are administered to a mammal other than a human, the time intervals should be adjusted accordingly based on the knowledge of the gastric cycles of the mammal of interest. Such adjustments can readily be made by one skilled in the art, e.g., a veterinarian or a person otherwise skilled in dealing with such mammals.

Various studies have been conducted in dog and in man to determine sizes of objects that would be retained in the stomach during the fed stage and also in the fasting stage when IMMC is present. Khosla and Davis, International Journal of Pharmaceutics, Vol. 62 (1990), pages R9-R11 have reported that a particle size less that 2 mm generally results in emptying from the stomach of the dog. Non-disintegrating tablets having sizes of 7, 11 and 13 mm in diameter were emptied from the human stomach, but the larger sized tablets tended to remain in the stomach longer than the small sized tablets. Tablets larger than 11 mm tended to be emptied only during the IMMC. Davis et al., Pharmaceutical Research, Vol. 8, No. 10 (1991) has described retention of radio-telemetry capsules having a size of 25×8 mm in the stomach of human subjects past phase 3 of the IMMC. Timmermans et al., Journal of Pharmaceutical Sciences, Vol. 82, No. 8 (1993) has reported the mean resting pyloric diameter in humans as 12.8±7.0 mm. Accordingly, it is important that gastric retentive delivery vehicles that are designed to achieve the preferred conditions that are suitable for delivering the compositions of the present invention are adapted to disintegrate, dissolve or erode to sizes that permit eventual elimination of the vehicle without causing gastric obstruction.

Various dosage forms have been described to provide active agent delivery devices that remain in the stomach for extended periods or time have been described. For example, U.S. Pat. No. 4,851,232 describes a hydrogel reservoir containing tiny pills having a active agent core surrounded by a wall controlling delivery of active agent to the stomach. The hydrogel swells in the stomach to facilitate retention of the active agent reservoir in the stomach over time. U.S. Pat. No. 4,871,548 describes a dosage form including a mixture of low and high number average molecular weight hydroxypropylmethylcellulose polymers and active agent that swells when in the stomach. U.S. Pat. No. 4,767,627 describes substantially planar devices formed of bioerodible polymer including active agent that may be compressed and folded for oral administration and then released and unfolded in the stomach, where the devices are to be retained over an extended period of time. The devices have a longest diameter of between 1.6 and 5 cm. U.S. Pat. No. 5,443,843 describes a plurality of compressible retention arms and an attached controlled release device which in the expanded form resists gastrointestinal transit. U.S. Pat. No. 5,007,790 describes a sustained release active agent dosage form in the form of a capsule or tablet that includes a plurality of hydrophilic water-swellable, cross-linked polymer particles that swell in the stomach to promote gastric retention and permit gastric fluid to penetrate the particles to dissolve active agent and deliver it to the stomach in the solution state. A plurality of particles are packed into a capsule for administration to a patient. U.S. Pat. No. 5,582,837 describes a dosage form similar to that of U.S. Pat. No. 5,007,790, without the use of a cross-linked hydrophilic polymer. The particles are described as slippery and soft, preferably spherical, and having dimensions on the order of 6 to 18 mm in the swollen state; a suitable number of particles can be packed into capsules.

Delivery devices can be adapted to remain in the stomach for a prolonged period and to deliver active agent in a controlled manner. Even though control over the delivery of active agents that are released from a highly swellable matrix, as described in WO 99/07342, may be achieved in many instances, a greater degree of control is possible when the retention function of the dosage form and the drug, or active ingredient delivery function of the dosage form are addressed individually. Many different systems have been suggested for controlled delivery of active agents from a dosage form over a prolonged period of time with no particular emphasis on retention of the dosage form in the stomach for a prolonged period. For example, U.S. Pat. No. 4,290,426 describes a cylindrical dispenser for releasing a beneficial agent into a fluid environment at a rate that is governed by the fluid induced relaxation of a polymeric agent contained within the dispenser.

Coated dosage forms have also been suggested for delivery of a controlled amount of a beneficial agent over a prolonged period of time. U.S. Pat. No. 5,256,440 describes a process for producing a film coated dosage form. A continuous groove is inscribed in a dosage form core. A latex film is coated onto the core, the groove defining a fixed zone and a detachable zone for the film. The detachable portion of the latex film detaches when it is exposed to the environment of use, thereby exposing a discrete portion of the dosage form core surface. The remainder of the film remains attached to the dosage form core. The exposed portion of the dosage form surface erodes and releases active agent to the environment of use.

Coated tablets for constant and prolonged active agent release are described in U.S. Pat. No. 4,839,177 and Conte et al., J. Controlled Release, Vol. 26, (1993) pages 39-47. Products of this technology are sold under the brand name GEOMATRIX™ Systems. They are swellable matrices that are coated or tableted with polymeric barrier layers. Release performances of the systems are modulated as a result of the reduction of the releasing surface exposed to the dissolution medium by the polymeric barrier layer coatings. As the extent of coating of the system's surface is increased, the release kinetics of the system shift toward constant release.

U.S. Pat. No. 5,780,057 describes a two or three layered tablet where at least one of the layers swells by contact with biological fluids to promote retention of the tablet in the stomach where the active ingredient may be slowly released. At least one of the layers acts as a barrier for a predetermined period of time to the active agent that is contained one of the other layers. U.S. Pat. No. 5,534,263 describes a dosage form useful for the prolonged delivery of an active agent formulation in the form of a matrix having two or more insoluble bands on the surface of the matrix. The exposed surfaces of the matrix erode in a manner that creates additional surface areas to provide for prolonged release of an active agent formulation with determined release profiles. U.S. Pat. No. 6,797,283 is directed to a multilayered dosage form which is adapted for retention in the stomach and useful for the prolonged delivery of an active agent using a multilayer core formed of polymer matrices that swell upon contact with the fluids of the stomach, wherein at least one layer of the multilayered dosage form includes an active agent and a portion of the polymer matrices are surrounded by a band of insoluble material to control retention in the stomach.

Additional oral, controlled-release dosage forms include elementary osmotic pumps, such as those described in U.S. Pat. No. 3,845,770, mini-osmotic pumps such as those described in U.S. Pat. Nos. 3,995,631, 4,034,756 and 4,111,202, and multi-chamber osmotic systems referred to as push-pull, push-melt and push-stick osmotic pumps, such as those described in U.S. Pat. Nos. 4,320,759, 4,327,725, 4,449,983, 4,765,989, 4,892,778, 4,940,465, 4,915,949 and 5,126,142.

As can be seen, technology and drug delivery forms are available in order to allow for the controlled administration of the DBM-containing composition to be temporally spaced apart from the controlled delivery of the calcium-containing composition to facilitate obtaining the benefits of these components, namely maintaining and/or improving bone health.

The compositions of the present invention preferably include an edible oil of vegetable or animal origin in combination with DBM. Preferred oils include vitamin E, fish oil and olive oil. Typically a suitable amount of vitamin E for use in combination with DBM is about 1 IU to about 1000 IU; preferably about 5 IU to about 500 IU; more preferably about 15 IU to about 200 IU; for example, about 5 IU to about 100 IU. Alternatively, and particularly for the convenience of preparing compositions in combination with DBM, useful amounts of vitamin E can be identified based on weight; in other words, typically about 2 mg to about 1000 mg; preferably about 5 mg to about 400 mg; most preferably about 5 mg to about 50 mg.

Other optional nutritional ingredients useful in the present invention, for example to be included with either the DBM-containing composition or the calcium-containing composition, or both, include, in particular, various other vitamins, minerals and mixtures of each and both. Reference to vitamins in the present invention is understood to include the various available forms of such vitamin, including salts, derivatives and isomeric forms, said isomeric forms being understood to include, where they exist, enantiomers, stereoisomers, and racemates. Other useful vitamins in addition to vitamin E include B vitamins, vitamin D, riboflavin, niacin, biotin, and pantothenic acid. Various useful forms of vitamin D are available including, for example, cholecalciferol (D3), ergocalciferol (D2), and their biologically active metabolites and precursors such as, 1-alpha-hydroxy Vitamin D, 25-hydroxy vitamin D, 1,25-dihydroxy vitamin D and the like. B vitamins include the hydrochloride and nitrate salts of thiamin and thiamin alkyl disulfides such as the prophyldisulfide, tetrahydrofurfuryl disulfide, o-benzoyl disulfide; the hydrochloride and nitrate salts are preferred. Other B vitamins include Folic acid, vitamins $B_{12}$ (cyanocobalamin) and $B_6$ Folic acid is intended to include all chemical derivatives of folic acid that function equivalently to folic acid, such as mono- and polyglutamyl folates, dihydro- and tetrahydrofolates, methyl and formyl folates. Vitamin $B_6$ is intended to include all chemical derivatives of vitamin $B_6$ that function equivalently to vitamin $B_6$. Vitamin $B_6$ can be selected from hydrochloride salts or 5-phosphates of pyridoxine, pyridoxamine, or pyridoxal. The preferred vitamin $B_6$ is pyridoxine hydrochloride. Vitamin $B_{12}$ is intended to include all chemical derivatives of vitamin $B_{12}$ that function equivalently to vitamin $B_{12}$. Sources of Vitamin $B_{12}$ are, for example, cyanocobalamin, methylcobalamin, adenosylcobalamin, hydroxocobalamin and the like. Cyanocobalamin is preferred.

Other vitamins and nutritional components include the following; riboflavin sources selected, for example, from crystalline riboflavin coenzyme forms of riboflavin such as flavin adenine dinucleotide, flavin adenine mononucleotide, riboflavin 5-phosphate and their salts; riboflavin is preferred. Niacin may comprise, for example, nicotinic acid, nicotinamide (niacinamide), the coenzyme forms of niacin such as nicotinamide adenine dinucleotide, and nicotinamide adenine dinucleotide phosphate; nicotinamide and nicotinic acid are particularly preferred. Biotin can be selected from oxybiotin, biocytin, biotinol and the like; biotin is preferred. Pantothenic acid sources can be in the form of salts such as calcium pantothenate or as panthenol; calcium pantothenate is preferred. Antioxidant vitamins such as vitamin E and vitamin C are useful. Vitamin E is intended to include all functionally equivalent forms of tocopherol; however, d-alpha-tocopherol, dl-alpha-tocopherol, and/or their esters including acetates and succinates (particularly the acetate form) generally can be used as a source for vitamin E. Other sources of vitamin E include beta-tocopherol, gamma-tocopherol, the tocotrienols and their esters, tocopheryl nicotinate, polymeric tocopherol and the like. Vitamin C is intended to include all forms of vitamin C such as L-ascorbic acid, D-ascorbic acid, DL-ascorbic acid, D-araboascorbic acid, dehydroascorbic acid, esters of ascorbic acid or their salts, and the like.

Another nutritional component includes one or more carotenoid compound. Over 600 carotenoid compounds have been identified, of which at least 40 have been isolated in foods. The most common, in descending order, are lycopene, β-carotene, β-cryptoxanthin, lutein, α-carotene, and zeaxanthin (see N. I. Krinsky, Ann. Rev. Nutr., 13: 561-587, 1993). B-carotene commonly comprises 20% of Vitamin A activity. Mixed carotenoids are included and this is intended to include a combination of at least two of the following carotenoids: α-carotene, β-carotene, lycopene, lutein, zeaxanthin, and cryptoxanthin. When mixed carotenoids are used the composition of the invention preferably includes three or more, four or more, five or more, and most preferably all six of the above-noted carotenoids. Vitamin K is useful and can be selected from Vitamin $K_1$ (phytonadione, phylloquinone) or Vitamin $K_2$ (menaquinone) and their salts and derivatives; Vitamin $K_1$ is preferred.

Typically the compositions of the present invention can further include pharmaceutically acceptable components such as lactose, glucose, sucrose, corn starch, potato starch, cellulose esters such as cellulose acetate, ethyl cellulose, magnesium stearate, calcium silicate, precipitated silica, talc, fatty acids such as stearic acid, microcrystalline cellulose, carnauba wax and the like or mixtures thereof. Diluents and other additives such as one or more pharmaceutically acceptable binding agents, fillers, supports, thickening agents, taste-improving agents, coloring agents, preservatives, stabilizers, regulators, emulsifiers, flow agents, absorbents, and the like or mixtures thereof may be used depending on the form of the composition employed, e.g., pill, tablet, capsule, etc. Additionally, the process of the invention comprises using conventional processing techniques for preparation of the administration form. The product can be made by either direct compression, or slugging some of the ingredients, milling the slugs, blending with remaining ingredients then compressing as appropriate. The product can also be made into tablets using the wet granulation technique, drying the wet mass, blending with other ingredients, then compressing into tablets. Reference is made to standard reference texts for such purposes, incorporated herein to the extent necessary, for the preparation of the dosage forms. For example, "The Theory and Practice of Industrial Pharmacy" by Lachman, Lieberman, and Kanig, Third Edition, copyright 1986; "Remington: The Science and Practice of Pharmacy," $20^{th}$ Edition, copyright 2000 (A. R. Gennaro, Ed.); and "Handbook of Pharmaceutical Excipients," Third Edition, copyright 2000 (A. H. Kibbe, Ed.).

Also, the compositions of the invention optionally can contain at least one additional mineral selected from the group consisting of chromium, copper, manganese, molybdenum, zinc, iron, boron, nickel, phosphorous, potassium, silicon, tin, vanadium, and the like, as well as iodine. Iron if present, can be in forms used in multivitamins, multiminerals and nutritional supplements, for example, ferrous fumarate, ferrous gluconate, ferrous sulfate, ferric acetate, carbonyl iron, and the like. A typical form of magnesium is magnesium oxide and of selenium is sodium selenate. Phosphorous may be particularly useful when used in the compositions of the invention and also in combination with calcium, as both substances are found in bone in significant quantities.

The minerals optionally employed in the invention are typically in salt form. Such salts can be any of the well known salts for the particular mineral of interest including carbonate, oxide, hydroxide, chloride, sulfate, phosphate, gluconate, lactate, acetate, fumarate, citrate, malate, amino acids, and the like for the cationic minerals and sodium, potassium, calcium, magnesium, and the like for the anionic minerals. However the particular salt used and the level will depend upon their interaction, if any, with other supplement ingredients.

Other optional additives may be incorporated in the compositions of the present invention. Such additives include: amino acids such as glutamic acid, L-glutamine, L-arginine, glycine, L-glutathione, L-lysine, tyrosine, proline, L-cysteine, choline, and the like; phosopholipids; tocotrienols; selected herbals such as green tea, garlic, ginseng, hawthorne, alfalfa, gingko, grape seed extract, and the like; coenzyme Q10; alpha lipoic acid, omega-3 and omega-6 fatty acids; fish oils such as eicosapentenoic acid, docosahexaenoic acid, and the like; β-sitosterol; β-sitostanol; red yeast rice, pectin, betaine HCl; glucosamine, including D-glucosamine hydrochloride, n-acetyl-d-glucosamine, and other glucosamine derivatives; chondroitin, including chondroitin sulfate A and chondroitin sulfate B, in which the sulfate is esterified in the 4- and 6-positions respectively; and the like. Combination compositions comprising DBM with glucosamine and/or chondroitin are preferred. Such combinations can be administered in a single form, e.g., a tablet or capsule, with DBM or in separate forms, with or without supplemental vitamins and/or minerals. When present in combination with a therapeutically effective amount of DBM, glucosamine and chondroitin can typically each be present at about 100 mg to about 10,000 mg; preferably about 100 mg to about 1,000 mg; more preferably about 200 mg to about 800 mg in a suitable dosage form, such as a tablet, pill, capsule and the like. Typically, the ratio of DBM to glucosamine or DBM to chondroitin or DBM to a mixture of glucosamine and chondroitin is about 1:100 to about 100:1; more preferably about 1:5 to about 1:25.

In general, regarding the additional vitamins, nutrients and additional minerals, it is preferred that, when such optional ingredients are present, the compositions of the invention contain at least about 3% of United States Reference Daily Intakes ("RDI"), if a particular ingredient is defined, as delineated in the Code of Federal Regulations (21 C.F.R. Chapter 1, Apr. 1, 1997), of each of the particular additional nutrient and/or additional minerals that are present; preferably about 25% to about 1400% of the R.D.I.; more preferably about 75% to 500% of the R.D.I; for example about 100% to about 250%. More particularly preferred amounts of each optional nutrient and each optional mineral are given in the following table (each of the recited ranges should be understood to include the word "about" preceding the recitation of each number):

| Component | Preferred | More Preferred |
|---|---|---|
| Vitamin A | 200 IU to 10000 IU | 2500 IU to 5000 IU |
| Vitamin D | 200 IU to 800 IU | 400 IU to 600 IU |
| Thiamin ($B_1$) | 0.06 mg to 12 mg | 1.5 mg to 7.5 mg |
| Riboflavin ($B_2$) | 0.068 mg to 13.6 mg | 1.7 mg to 8.5 mg |
| Vitamin E | 10 IU to 500 IU | 15 IU to 150 IU |
| Pantothenic acid | 0.4 mg to 800 mg | 10 mg to 500 mg |
| Niacin | 0.8 mg to 160 mg | 20 mg to 100 mg |
| Biotin | 12 mcg to 800 mcg | 20 mcg to 300 mcg |
| Chromium | 4.8 mcg to 960 mcg | 25 mcg to 600 mcg |
| Copper | 0.08 mg to 9 mg | 1 mg to 6 mg |
| Iodine | 6 mcg to 1200 mcg | 150 mcg to 750 mcg |
| Manganese | 0.08 mg to 10 mg | 2 mg to 8 mg |
| Molybdenum | 3 mcg to 350 mcg | 75 mcg to 250 mcg |
| Zinc | 0.6 mg to 60 mg | 15 mg to 30 mg |
| Boron | >0 mcg to 1200 mcg | >0 mcg to 750 mcg |
| Chloride | >0 mg to 12000 mg | >0 mg to 8000 mg |
| Nickel | >0 mcg to 40 mcg | >0 mcg to 25 mcg |
| Phosphorus | >0 mg to 4000 mg | >0 mg to 2400 mg |
| Potassium | >0 mg to 6000 mg | >0 mg to 4000 mg |
| Silicon | >0 mg to 50 mg | >0 mg to 10 mg |
| Tin | >0 mcg to 80 mcg | >0 mcg to 50 mcg |
| Vanadium | >0 mcg to 80 mcg | >0 mcg to 50 mcg | mcg = microgram or $10^{-6}$ grams, also written as µg
IU = international unit; an internationally agreed to unit of measurement based on measured biological activities.

All of the amounts and ranges of ingredients of the compositions of the invention given herein are on a per dose basis. A single dose of the compositions is typically suitable for the daily requirements of most patients, although in some situations multiple doses per day are indicated. Most preferably, the dose is contained in one or two dosage units.

The compositions of the present invention can include other nutritionally beneficial vitamins, minerals and compounds, including for example, methylsulfonyl methane (MSM), S-adenosyl methionine (SAMe), isoflavone, and the like.

Those skilled in the art will take care to select optional additional compounds, ingredients, additives and/or the amounts thereof, such that the advantageous properties, in particular the bone improving and other properties associated with the DBM nutritional supplement in accordance with the invention, are not, or are not substantially, adversely affected by the addition(s) envisioned.

In another embodiment of the invention, bone health is maintained in a mammal by providing as a nutritional supplement a therapeutically effective amount of DBM on a periodic basis. Depending on the condition of the mammal to which the composition is administered, the period can be as frequent as daily or multiple times per day, e.g., about 2 to about 4 times per day or more; or as infrequent as weekly, twice per month, monthly, etc. For example, an oral administration schedule can include a frequency selected from the group consisting of twice per day, once per day, once every two days, once every three days, once every four days, once every five days, once every six days, once per week, twice per week, three times per week, four times per week, twice per month, and once per month.

In further embodiment of the invention, an article of manufacture is provided which contains the composition(s) of the present invention and provides instructions for its use. The article of manufacture comprises a container. Suitable containers include, for example, bottles and vials including dual chamber vials. The container may be formed from a variety of materials such as glass or plastic. The container holds the composition in a suitable form or forms including tablets and capsules and the label on, or associated with, the container may indicate directions for use. For example, the label may indicate that the administerable form is to be taken at specified time intervals and in specified numbers. The container holding the composition(s) may be a multi-use vial, which allows for repeat administrations of the compositions. The article of manufacture may further comprise a second container comprising such that the compositions of the invention are separately provided as a DBM-containing composition and a calcium-containing composition. The article of manufacture may further include other materials desirable from a commercial and user standpoint, including other package inserts with instructions for use.

In the specification and claims the term "about" when used as a modifier for, or in conjunction with, a variable, characteristic or condition is intended to convey that the numbers, ranges, characteristics and conditions disclosed herein are flexible and that practice of the present invention by those skilled in the art using temperatures, concentrations, amounts, contents, carbon numbers, properties such as purity, particle size, surface area, bulk density, etc., that are outside of the range or different from a single value, will achieve the desired result, namely, a nutritional composition or supplement comprising DBM in a form typically suitable for ingestion and suitable for maintaining and/or improving the bone or cartilage health of an individual.

As used throughout the specification and claims, including the described embodiments, the singular forms "a," an," and "the" include plural referents unless the context clearly dictates otherwise. Thus, for example, reference to "an osteoinductive growth factor (OGF)" includes a single OGF as well a two or more different OGFs in combination, and the like.

The following examples are provided as specific illustrations of embodiments of the claimed invention. It should be understood, however, that the invention is not limited to the specific details set forth in the examples. All parts and percentages in the examples, as well as in the specification, are by weight unless otherwise specified. Any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% ... 50%, 51%, 52% ... 95%, 96%, 97%, 98%, 99%, or 100%. Moreover, any numerical range represented by any two values of R, as calculated above is also specifically disclosed.

EXAMPLES

Example 1

Preparation of Demineralized Bone Matrix

Bones from a suitable source, e.g., bovine or porcine, are cleaned to remove extraneous tissue, e.g., by hand or mechanical scraping, and the cleaned bones are coarsely cut into convenient sizes for further size reduction and grinding using a hammer mill type comminution mill; preferably the bone grinding operation is carried out as a wet operation. The ground bone powder is wet sieved to remove large size pieces using deionized water. The ground bone powder is then demineralized using 0.6M HCl. The acidified mixture is agitated for about 30 minutes to about 2 hours. The demineralized bone powder is rinsed with deionized water to remove traces of acid. The rinsed DBM is rinsed with 70% alcohol (either ethanol or isopropanol being suitable) and filtered to obtain a wet product which is subsequently dried using air, oven, vacuum, lyophilization or a combination of these methods. Thereafter the product is placed in a suitable container, preferably a moisture tight container.

Example 2

Preparation of Compositions of the Invention

Mixtures of the following ingredients are prepared and formed into tablets using standard commercial tableting methods.

Calcium-Containing Compositions

Composition A

| Item | Ingredient | mg/tablet |
|---|---|---|
| 1 | Calcium citrate | 500 |
| 2 | Magnesium oxide/citrate | 200 |
| 3 | Vitamin D3 | 200 IU |

Composition B

| Item | Ingredient | mg/tablet |
|---|---|---|
| 1 | Calcium citrate | 500 |
| 2 | Magnesium oxide/citrate | 200 |
| 3 | Boron | 1 |
| 4 | Selenium | 25 mcg |
| 5 | Vitamin C | 60 |
| 6 | Vitamin B6 | 1 |
| 7 | Vitamin B12 | 3 mcg |
| 8 | Vitamin D3 | 200 IU |

Demineralized Bone Matrix (DBM)-Containing Compositions

The DBM prepared in Example 1 is mixed with the additional ingredients listed below and formed into tablets or capsules, as appropriate, using standard commercial methods. Typically, where vitamin E is present, a capsule is used.

Composition A

| Item | Ingredient | mg/tablet |
|---|---|---|
| 1 | DBM | 150 |
| 2 | Vitamin E | 15 IU |

Composition B

| Item | Ingredient | mg/tablet |
|---|---|---|
| 1 | DBM | 200 |
| 2 | Vitamin E | 20 IU |

Composition C

| Item | Ingredient | mg/tablet |
|---|---|---|
| 1 | DBM | 50 |
| 2 | Glucosamine HCl | 500 |
| 3 | Chondroitin sulfate | 400 |
| 4 | Fish oil/cod liver oil | 50 |

Composition D

| Item | Ingredient | mg/tablet |
|---|---|---|
| 1 | DBM | 80 |
| 2 | Glucosamine HCl | 1000 |
| 3 | Chondroitin sulfate | 1000 |
| 4 | Olive oil | 80 |

Composition E

| Item | Ingredient | mg/tablet |
|---|---|---|
| 1 | DBM | 150 |
| 2 | Vitamin E | 15 IU |

Composition F

| Item | Ingredient | mg/tablet |
|---|---|---|
| 1 | DBM | 150 |
| 2 | Vitamin E | 15 IU |
| 3 | Gelatin | 1000 |

Composition G

| Item | Ingredient | mg/tablet |
|---|---|---|
| 1 | DBM | 150 |
| 2 | Vitamin E | 15 IU |
| 3 | methylsulfonylmethane (MSM) | 500 |

Composition H

| Item | Ingredient | mg/tablet |
|---|---|---|
| 1 | DBM | 150 |
| 2 | Vitamin E | 15 IU |
| 3 | S-adenosyl methionine (SAMe) | 400 |
| 4 | Isoflavone | 40 |

All documents, including patents, described herein are incorporated by reference herein, including any priority documents and/or testing procedures. The principles, preferred embodiments, and modes of operation of the present invention have been described in the foregoing specification. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A nutritional supplement, comprising demineralized bone matrix (DBM) derived from a source of bone comprising native bone-active substances
   wherein said native bone-active substances in said source of bone comprise native Bone Morphogenic Proteins, (BMPs) and native Transforming Growth Factors-beta, (TGF-beta),
   said DBM comprising at least one native bone active substance selected from the group consisting of native Bone Morphogenic Proteins, (BMPs) and native Transforming Growth Factors, (TGF-beta),
   wherein said DBM, BMPs and TGF-beta are in therapeutically effective amounts to manage a bone or joint condition or bone or joint health in a subject, and wherein, said supplement being orally administrable to a subject.

2. The supplement of claim 1 comprising at least one BMP wherein said DBM comprises between about 0 to about 6 wt % native calcium.

3. The supplement of claim 2 comprising at least one of an orally ingestible pharmaceutically acceptable carrier, filler or excipient.

4. The supplement of claim 3 comprising about 50 mg to about 800 mg of DBM.

5. The supplement of claim 3 wherein said bone active substance is native BMP.

6. The supplement of claim 3 further comprising at least one vitamin, including salts, isomeric forms and derivatives of said vitamin.

7. The supplement of claim 6 wherein said at least one vitamin is selected from the group consisting of vitamin D, vitamin E, B vitamins; vitamin K; carotene-containing compounds; and combinations thereof.

8. The supplement of claim 2 wherein said DBM comprises collagen type I and collagen type II and at least one member selected from the group consisting of TGF-β2, TGF-β1, BMP-2, BMP-3, BMP-4, BMP-5, BMP-6, BMP-7, BMP-8, BMP-9, BMP-10, IGF-I, IGF-II, PDGF-AA, PDGF-BB, PDGF-AB, β-FGF and VEGF.

9. The supplement of claim 7 wherein said at least one vitamin is vitamin E.

10. The supplement of claim 9 wherein said vitamin E is present at about 5 IU to about 500 IU.

11. The supplement of claim 3 in an orally administrable unit dosage form wherein said supplement is for oral administration to a mammal.

12. The supplement of claim 11 wherein said mammal is a human.

13. The supplement of claim 12 wherein the source of bone from which the DBM is derived is bovine, porcine or other farm animal.

14. The supplement of claim 13 wherein said source bone is bovine.

\* \* \* \* \*